United States Patent [19]

Buehler et al.

[11] Patent Number: 4,800,086

[45] Date of Patent: Jan. 24, 1989

[54] PREPARATION OF ASCORBIC ACID GRANULES

[75] Inventors: Volker Buehler, Wachenheim; Friedbert Hofmann, Neuhofen; Robert Heinz, Mannheim, all of Fed. Rep. of Germany

[73] Assignee: BASF Aktiengesellschaft, Fed. Rep. of Germany

[21] Appl. No.: 810,372

[22] Filed: Dec. 18, 1985

[30] Foreign Application Priority Data

Dec. 24, 1984 [DE] Fed. Rep. of Germany ....... 3447422

[51] Int. Cl.⁴ .............................................. A61K 9/16
[52] U.S. Cl. ...................................... 424/497; 424/80
[58] Field of Search ................ 424/465, 80, 497, 3

[56] References Cited

U.S. PATENT DOCUMENTS 2,820,741  1/1958  Endicott et al. ...................... 167/82
4,036,948  7/1977  Kitamori et al. ............... 424/494 X
4,203,997  5/1985  Kuppers et al. ..................... 424/280

FOREIGN PATENT DOCUMENTS 49143   4/1982  European Pat. Off. .
2380777 9/1928  France .
844772  8/1960  United Kingdom .

OTHER PUBLICATIONS

Peter C. Schmidt, Deutsche Apotheker Zeitung, 122 Jahrg. Nr. 3, (1982), p. 111, FIG. 12, and p. 110, Top of Right Column.

S. P. Gladkikh, Khimiko-Farmatsevticheskii Zhurnal, vol. 4, No. 12, pp. 37–42, Dec. 1970.

S. Lee et al., J. Pharm. Sci. 54 (1965), No. 8, p. 1156, Table VI.

*Primary Examiner*—Michael Lusignan
*Attorney, Agent, or Firm*—Keil & Weinkauf

[57] ABSTRACT

Ascorbic acid granules for direct tableting are prepared by the compacting method, wherein the ascorbic acid in the form of crystals or crystal fragments, of which not more than 40% by weight have a longest particle diameter of less than 50 μm and not more than 15% by weight have a longest particle diameter greater than 500 μm, and as a mixture with from 0.8 to 8% by weight of soluble polyvinylpyrrolidone having a water content of from 0.3 to 5% is compacted in a conventional manner, and the product is comminuted.

2 Claims, No Drawings

PREPARATION OF ASCORBIC ACID GRANULES

The present invention relates to a process for the preparation of ascorbic acid granules for direct tableting with polyvinylpyrrolidone (PVP) as a binder, by the compacting method. These granules can be converted to stable tablets.

In order to press ascorbic acid in fairly high concentration to tablets, granulation with a binder has to be carried out beforehand. PVP is one of the suitable binders, having a very high binding power and at the same time imparting a high disintegration rate to the tablets prepared from the granules. It has the further advantage of being water-soluble, which is important, for example, for use in efferverscent tablets. However, it is known that ascorbic acid granulated with PVP results in unstable tablets, and that water greatly reduces the stability (Peter C. Schmidt, Deutscne Apotheker Zeitung 122 (1982) No. 3, page 111, FIG. 12, and page 110, top of right-hand column). It has therefore been recommended that granulation be carried out using anhydrous solvents (S.P. Gladkikh, Khimiko-Farmatsevticheskii Zhurnal, Vol. 4, No. 12, pages 37–42, December 1970, Engl. translation 1971, Consultants Büro, A Division of Plenum Publishing Corporation, 227 West 17th Street, New York, N.Y. 10011, page 702, paragraph 6). The fact that the tablets tend to become yellowish to brownish even before any marked loss of activity occurs is particularly troublesome. S. Lee et al. (J. Pharm. Sci. 54 (1965), No. 8, page 1156, Table VI) have shown that when PVP is employed as a binder even the use of anhydrous solvents does not lead to stable granules. Moreover, for reasons of environmental protection, the use of organic solvents is avoided nowadays as far as possible.

Other binders, ie. starch and ethyl cellulose, are used in commercial granules of ascorbic acid for direct tableting. These binders too do not always give granules having a stable color, and in particular the disintegration properties and the water solubility of the tablets are poorer when these binders are used instead of PVP.

It is an object of the present invention to provide a process for the preparation of ascorbic acid granules which have a stable color, contain PVP as a binder and can be directly tableted. Here, color stability means that the granules show no discoloration, or virtually no discoloration, when stored in a closed container for not less than one year at room temperature or 3 months at 40° C. Storage in a closed container means that an airtight seal is employed, and not that air is absent. Direct tableting means that the material can be pressed to tablets with or without being mixed with other auxiliaries and without granulation.

We have found that this object is achieved by a process for the preparation of ascorbic acid granules for direct tableting by the compacting method, wherein the dry ascorbic acid containing less than 0.3% of water and having a particle size of from 30 to 500 $\mu$m, preferably from 50 to 250 $\mu$m, as a mixture with from 0.8 to 8, preferably from 1 to 6, % by weight, based on the ready-prepared granules, of soluble PVP having a water content of from 0.3 to 5, preferably from 0.5 to 4, % by weight, based on the PVP, is compacted in a conventional manner, and the product comminuted. Not more than half the soluble PVP may be replaced with finely divided, preferably micronized, insoluble PVP having a water content in the same range.

During compacting, the mixture of the active compound (in this case ascorbic acid) and the binder, and if required further auxiliaries, is compressed to a strand between two rollers and then comminuted, and (at least in the process of the present invention) the fraction having particle diameters of from 100 to 1000 $\mu$m, preferably from 200 to 800 $\mu$m, is used for the preparation of tablets, and the finer and coarser fractions are once again used in the compacting process.

The addition of finely divided (100% by weight of the particles smaller than 100 $\mu$m), preferably micromized (100% by weight of the particles smaller than 50 $\mu$m and 90% by weight smaller than 10 $\mu$m), insoluble (prepared by popcorn polymerization, ie. predominantly physically crosslinked) PVP has proven particularly useful with regard to the color stability but has the disadvantage (which is only important in the case of effervescent tablets) that the product does not dissolve in water to give a clear solution. Soluble PVP has a K value of from 20 to 95, preferably from 28 to 95, according to the British Pharmacopeia 1980, Addendum 1982, page 93.

When the granules are pressed to tablets, the conventional auxiliaries may be used, for example additional binders, such as starch, cellulose, dextrin or amylopectin, all of which may be chemically modified, or gelatine or tragacanth; fillers, such as calcium sulfate, amylose, lactose or cellulose; tartaric or citric acid and sodium bicarbonate for effervescent tablets; lubricants, such as talc, magnesium stearate or calcium stearate, if necessary mixed with corn starch, wax-like substances, eg. saturated fatty acids or a hydrogenated glycerol as a mixture with a stearate and/or titanium dioxide, polyethylene glycol, silica gel or calcium arachinate; flavorings, such as saccharin, cyclamate or sugar, or aromas, such as vanillin or orange extract, and dyes and antioxidants. The tablets may also be coated.

The ascorbic acid granules for direct tableting which are prepared according to the invention are superior, in some cases substantially superior, to similar commercial products with regard to the color stability of the granules themselves and of the tablets prepared from them. Moreover, tablets prepared from the novel granules in accordance with conventional formulations disintegrate in simulated gastric juice in a substantially shorter time than that taken by tablets prepared in the same manner from commercial granules. Finally, when insoluble PVP is omitted, the novel granules, in contrast to commercial ones, are suitable for the preparation of effervescent tablets which dissolve to give a clear solution, the abovementioned advantages substantially being retained.

In the Examples, parts are by weight

EXAMPLE 1

Preparation

| | |
|---|---|
| Ascorbic acid (not more than 10% by weight having a particle size greater than 150 $\mu$m, not less than 65% by weight having a particle size greater than 50 $\mu$m) | 96 kg |
| Soluble polyvinylpyrrolidone (K value 28-32, water content 1.6%) | 4 kg |

The homogeneous mixture was compacted in dry form, and the product comminuted. The coarse fraction above 1000 $\mu$m was removed by screening.

Stability

In contrast to the commercial ascorbic acid granules for direct tableting, the resulting compacted material showed no color change at all after storage in an airtight container at 40° C. for 3 months. The content of ascorbic acid also did not change.

Use

The compacted material was compared with the commercial granules by direct tableting of the following formulation for effervescent tablets:

| Compacted ascorbic acid or ascorbic acid granules | 1000 mg |
|---|---|
| Powdered tartaric acid | 200 mg |
| Sorbitol | 200 mg |
| Sodium bicarbonate | 172 mg |
| Polyethylene glycol having a mean molecular weight of 6000 | 60 mg |

The effervescent tablets (20 mm diameter, biplanar, produced using a compacting pressure of 50 kN) had the following properties:

| Product | Hardness | Disintegration in water | Abrasion* |
|---|---|---|---|
| Compacted material (Example 1) | 140 N | 2–3 min | 0.1% |
| Commercial granules | 150 N | 9 min | 0.2% |

The effervescent tablets prepared from the compacted material had a more stable color than most of the comparative preparations and dissolved in water to give a clear solution, in contrast to the effervescent tablets prepared from the commercial granules.

EXAMPLE 2

Preparation

| Ascorbic acid (not more than 10% by weight having a particle size greater than 150 μm, not less than 65% by weight having a particle size greater than 50 μm) | 96 kg |
|---|---|
| Soluble polyvinylpyrrolidone (K value 30, water content 1.6%) | 3 kg |
| Insoluble, micronized polyvinylpyrrolidone (water content 3.5%) | 1 kg |

Processing has carried out as in Example 1.

Stability

The resulting compacted material had the same stability as the compacted material obtained in Example 1.

Use

The compacted material was compared with the commercial granules using the following tablet formulation:

| Compacted ascorbic acid or ascorbic acid granules | 300 mg |
|---|---|
| Microcrystalline cellulose | 200 mg |
| Polyethylene glycol 6000 | 20 mg |
| 8:1:1 Mixture of talc, silica gel and calcium arachinate | 5 mg |

The tablets (12 mm diameter, biplanar faceted, produced using a compacting pressure of 10 kN) had the following properties:

| Starting material | Hardness | Disintegration time in simulated gastric juice | Abrasion* |
|---|---|---|---|
| Compacted material according to the invention | 115 N | 90 sec | <0.1% |
| Commercial granules | 130–150 N | 19–20 min | <0.1% |

*Hoffman-LaRoche friabilator

EXAMPLE 3

| Ascorbic acid (not less than 65% by weight having a particle size greater than 150 μm, not more than 5% by weight having a particle size greater than 500 μm) | 98 kg |
|---|---|
| Soluble polyvinylpyrrolidone (K value 90, water content 3.1%) | 1 kg |
| Insoluble, micronized polyvinylpyrrolidone (water content 3.5%) | 1 kg |

Processing was carried out as in Example 1.

We claim:

1. A process for the preparation of ascorbic acid granules which have a stable color and which can be directly tableted hich comprises: mixing crystals or crystal fragments of ascorbic acid containing less than 0.3% water, with from 0.8 to 8% by weight of soluble polyvinylpyrrolidine, having a water content of 0.3 to 5% by weight, wherein not more than 40% by weight of said ascorbic acid crystals or crystal fragments have a longest particle diameter of less than 50 μm, and not more than 15% by weight have a longest particle diameter greater than 500 μm; compressing the mixture of ascorbic acid crystals or crystal fragments and polyvinylpyrrolidone to form a strand, and comminuting the strand to form granules of ascorbic acid and polyvinylpyrrolidone.

2. A process for the preparation of ascorbic acid granules as claimed in claim 1, wherein up to one half the soluble polyvinylpyrrolidone is replaced with insoluble polyvinylpyrrolidone.

* * * * *